(12) United States Patent
Darling et al.

(10) Patent No.: US 7,851,210 B2
(45) Date of Patent: *Dec. 14, 2010

(54) APPARATUS FOR RECYCLING OF PROTEIN WASTE AND FUEL PRODUCTION

(76) Inventors: Jonathan Scott Darling, 311 Ivan, Pender, NE (US) 68047; Don Scott Darling, 311 Ivan, Pender, NE (US) 68047

( * ) Notice: Subject to any disclaimer, the term of this patent is extended or adjusted under 35 U.S.C. 154(b) by 952 days.

This patent is subject to a terminal disclaimer.

(21) Appl. No.: 11/706,123

(22) Filed: Feb. 14, 2007

(65) Prior Publication Data

US 2007/0212776 A1    Sep. 13, 2007

Related U.S. Application Data

(63) Continuation-in-part of application No. 10/607,691, filed on Jun. 30, 2003, now Pat. No. 7,226,778.

(51) Int. Cl.
| | |
|---|---|
| C12M 1/00 | (2006.01) |
| C12M 3/00 | (2006.01) |
| C07K 1/00 | (2006.01) |
| A23L 1/31 | (2006.01) |

(52) U.S. Cl. .............. 435/289.1; 435/290.1; 435/290.4; 435/262; 435/262.5; 435/272; 71/11; 71/15; 71/18; 99/483; 426/54; 426/55; 426/56; 426/53; 426/59

(58) Field of Classification Search .............. 435/289.1, 435/290.1, 290.4, 262.5, 272, 262; 71/11, 71/15, 18; 99/483; 426/54, 55, 59, 53, 56

See application file for complete search history.

(56) References Cited

U.S. PATENT DOCUMENTS

| | | | |
|---|---|---|---|
| 4,908,220 A | 3/1990 | Shih et al. | |
| 4,959,311 A | 9/1990 | Shih et al. | |
| 5,162,129 A * | 11/1992 | Anderson et al. | 426/657 |
| 5,352,469 A * | 10/1994 | Peters | 426/478 |
| 5,713,788 A | 2/1998 | Ferket et al. | |
| 6,045,070 A * | 4/2000 | Davenport | 241/60 |
| 6,299,774 B1 * | 10/2001 | Ainsworth et al. | 210/603 |
| 6,474,576 B1 * | 11/2002 | Oota et al. | 241/34 |
| 6,958,110 B2 * | 10/2005 | Sermanni et al. | 162/237 |

* cited by examiner

*Primary Examiner*—Nathan A Bowers
(74) *Attorney, Agent, or Firm*—G. Brian Pingel; Camille L. Urban (57) ABSTRACT

The apparatus of the present invention is useful for recycling protein waste and producing fuel from protein waste. Waste is ground by a grinding means and digested by a enzyme digest medium composed of enzymes, preservatives, and inedible egg. The ground proteins are digested with the enzyme in recirculated digest tanks. Fat can be collected from the tank by addition of acid and separation of fat from water with a centrifuge. Alternatively the ground protein and enzyme can be fermented and gas collected from the digest tank in a pressure tank with a compressor. The protein solubles are emulsified, separated from water, and extruded before drying. Either fat or gas can be used to fuel a dryer. The dried proteins are then milled in a hammer mill and screened for uniform size.

26 Claims, 9 Drawing Sheets

APPARATUS FOR RECYCLING OF PROTEIN WASTE AND FUEL PRODUCTION

This is a Continuation-In-Part of application Ser. No. 10/607,691 filed Jun. 30, 2003 now U.S. Pat. No. 7,226,778.

BACKGROUND OF INVENTION

1. Field of the Invention

The present invention relates in general to naturally recycling protein waste into feed and, more specifically, to an apparatus and process for enzymatically digesting, emulsifying and drying protein waste including feathers for use in animal feed.

2. Description of the Prior Art

A mass of waste is accumulated on a regular basis in such operations as poultry production facilities. Protein waste such as carcasses from animal production facilities pose problems for disposal. Carcasses are currently disposed of in many ways including land filling and burning. Natural gas production from waste materials is also known in the art and such processes typically also result in a byproduct which is used as animal feed or fertilizer. Some facilities process the protein waste to produce a component for animal feed but these plants often are not designed to provide a mostly closed system and, consequently, air, moisture, and other contaminants may enter creating an environment where microorganisms can multiply and destroy the quality or usefulness of the processed protein waste.

And, although there may be processing plants at which protein waste may be disposed and recycled, there is not an efficient way to remove the waste from the site to the processing plant in such time and condition as necessary for efficient processing. The timing of such disposal is essential to managing toxicity and odors yet it is not feasible for each animal production plant to also operate a processing plant for its protein waste.

Animal feed requires a protein component. In addition to the carcasses which can be processed for protein recovery, feathers are inexpensive and also high in protein, however, feathers are difficult for animals to digest And, although there are processes known for forming feather meal, often these processes require steam which, if too hot, will denature the proteins in the feathers and reduce their nutritional values. It is also known that certain bacterial strains produce keritinase which is an enzyme capable of degrading feathers and that, properly employed, such degradation can result in material that can be used in animal feeds. See U.S. Pat. Nos. 4,908, 220; 4,959,311.

In addition, it is known in the art to provide a means to grind swine or poultry waste and then mix it with ingredients that will facilitate fermentation of the protein waste. See U.S. Pat. No. 5,713,788. The invention disclosed therein provides a specific grinding mechanism which includes a grinding drum with a helical groove on its outer surface in which a length of chainsaw chain, teeth side out, is positioned. This invention also does not include a way to re-circulate and thoroughly mix the ground protein and catalyst but, instead, depends on a metered application of catalyst to the ground protein waste as it moves past the grinder wherein the metering of the catalyst is triggered by the load on the grinder. This is deficient in that no additional mixing of the ground protein waste and catalyst is contemplated such that there is substantial risk that it will not be appropriately mixed and the catalytic action will be hampered.

What is needed is a way for the animal production facilities to efficiently and timely dispose of animal waste in such a way that is non-toxic and odor free. In addition, the system has to be affordable for the animal production facilities and the resultant recycled product must be usable. Preferably, a mostly closed system should be used to eliminate environmental contaminants and to provide avenues for recycling by-products. Finally, for any disposal of feathered animals, the system must provide a method of breaking down not only softer protein sources, but also feathers and in a manner that does not denature or destroy the food value of the proteins.

The first objective of the present invention is to provide a system wherein animal protein waste is processed in such a way that a portion of the system may be mobile and can be taken from one animal production facility to another or simply positioned at one facility until it reaches capacity;

The second objective of the present invention is to provide a protein processing system which is capable of degrading feathers without destroying their food value;

The third objective of the present invention is to provide a way for many different and maybe distant animal production facilities to have routine access to a processing facility;

The fourth objective of the present invention is to use means for recycling and breaking down the animal protein wastes and to recycle by-products of the process;

The fifth objective of the present invention is to provide an apparatus that provides mixing and grinding capabilities associated with one another in a manner that results in a mostly closed system which is an efficient process for digesting, emulsifying and drying the recycled protein waste while also providing a means for recycling other byproducts such as water and for minimizing growth of damaging microorganisms.

The sixth objective of the present invention is to provide an apparatus for recycling animal protein that produces fuel from the digesting or fermentation of animal protein waste.

The Seventh objective of the present invention is to provide an apparatus for animal protein recycling that produces fuel and uses the produced fuel to power portions of the apparatus.

SUMMARY

The present invention provides an apparatus and process for naturally recycling poultry carcasses for use as a nutritional supplement. The apparatus generally has four modules: (1) a pH adjustable enzymatic digest medium mixing assembly, (2) a mobile grinding assembly mounted on a truck trailer; (3) a digesting and emulsifying assembly which includes a heated tank and separator or alternatively a fermentation assembly; and (4) a drying system.

The enzymatic digest medium of the preferred embodiment includes protease/keritinase, inedible egg, water, and a preservative. The amount of preservative to be added to the medium can be determined by a circuit using data from a load sensor on the grinding means to control a variable frequency drive which controls the speed of a preservative pump. The digest medium mixing assembly is equipped with a pH probe and monitor which triggers the addition of an acidic solution as needed to adjust the pH of the enzymatic digest.

The mobile grinding assembly can be moved from one animal production facility to another or can remain at one facility. The mobile grinding assembly of the preferred embodiment is mounted on a trailer and includes a holding tank for the enzymatic digest medium and a conveyor for loading carcasses into a grinder. The remainder of the grinding assembly is a closed system. Once through the grinder, the ground carcasses are pumped into a storage tank with the enzymatic digest medium to produce a protein solubles mixture. This mixture is then recirculated through a chopper pump for a few minutes to further reduce particle size of the ground protein waste and assure adequate mixing of the digest and the proteins and then pumped into a tanker truck for transport. Multiple batches of the protein solubles mixture can be generated so that the storage tanks are filled and emptied as many times as necessary until all the waste has been disposed. Then, the mobile grinding assembly can be moved to another location or it can simply remain until it is needed again.

The protein solubles mixture created by the mobile grinding assembly is then moved to a centralized and stationary processing plant and transferred from the tanker truck to the digesting and emulsifying assembly. The enzyme digest in the protein solubles mixture works best between about 100 and 130 degrees Fahrenheit. Therefore, the digesting and emulsifying assembly heats the mixture if needed and only periodically recirculates it until the enzymatic digest has altered the protein solubles to a mostly liquid state. The digested protein solubles are then run through an emulsifier to completely disperse the fats and proteins. The digested and emulsified proteins are then pumped into a separator tank and the bottom layer of water is drained off periodically, leaving the emulsified proteins. The water layer is then recycled back to the portion of the system where the enzymatic digest is made. The remaining emulsified proteins are then transferred to the drying system.

Fats can be collected from the digest and emulsification assembly via a closeable connection and a first fats tank. Fats can be separated from the protein solubles mixture by addition of acid from an acid tank via a pump. A valve on the recirculation means closes to allow transfer of fats from the digest tank through an open closeable connection. Fats in the first fats tank are separated from water in a centrifuge and stored in a second fats tank. The water collected is recycled back into the digester tank.

In alternative to the digest and emulsification assembly, the apparatus can include a fermentation assembly. In the fermentation assembly the protein solubles mixture is brokendown by bacteria which produces gas. Gas is collected by a piping and compressed by a compressor into a pressure tank. Check valves along the piping prevent backflow of gas. The compressor is controlled by a pressure sensor on the fermentation tank.

The dryer system uses a carrier for surface absorption of moisture, extrusion, air flow, and heat to accomplish the removal of moisture. A carrier such as cereal, soybean meal, corn or wheat mids is fed through a volumetric feeder to a mill where it is finely ground to provide ample surface area for absorption. The carrier is then conveyed to a mixer where it is mixed with the emulsified proteins until a doughlike consistency is reached. At this point, the dough is fed into an extruder to remove additional moisture and to extrude dough pellet-like pieces which are then moved by oscillating belt to the drying apparatus.

The drying apparatus includes a dryer bed which, in the preferred embodiment, is a conveyor belt enclosed in a housing. The housing alternates air flow direction and has heat zones for removing yet more moisture content and a cooling zone to return the pellet-like pieces to near room temperature. The pellet-like pieces are moved progressively through the air flow, the heat zones and the cooling zone by the conveyor. Next, the pellet-like pieces are sized and then run over a vibrating screen to separate the non-uniform sized pieces. Finally, the appropriately and uniformly sized pellet-like pieces are packaged.

Other objects, features, and advantages of the present invention will be readily appreciated from the following description. The description makes reference to the accompanying drawings, which are provided for illustration of the preferred embodiment. However, such embodiment does not represent the full scope of the invention. The subject matter which the inventor does regard as his invention is particularly pointed out and distinctly claimed in the claims at the conclusion of this specification.

DESCRIPTION OF THE PREFERRED EMBODIMENT(S)

Figure 1:
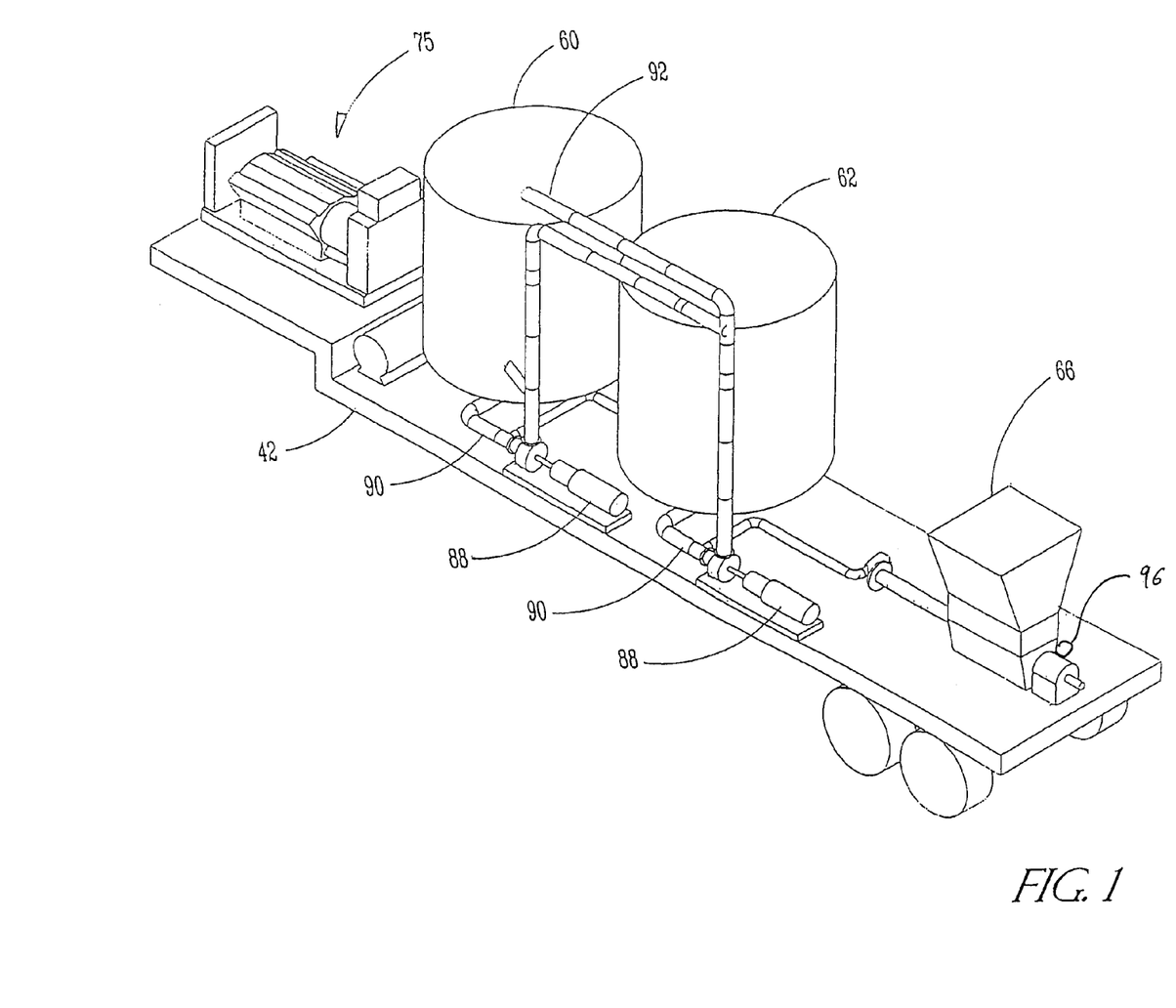
FIG. 1 is a perspective view of the mobile grinding assembly portion of the present invention.
Figure 2:
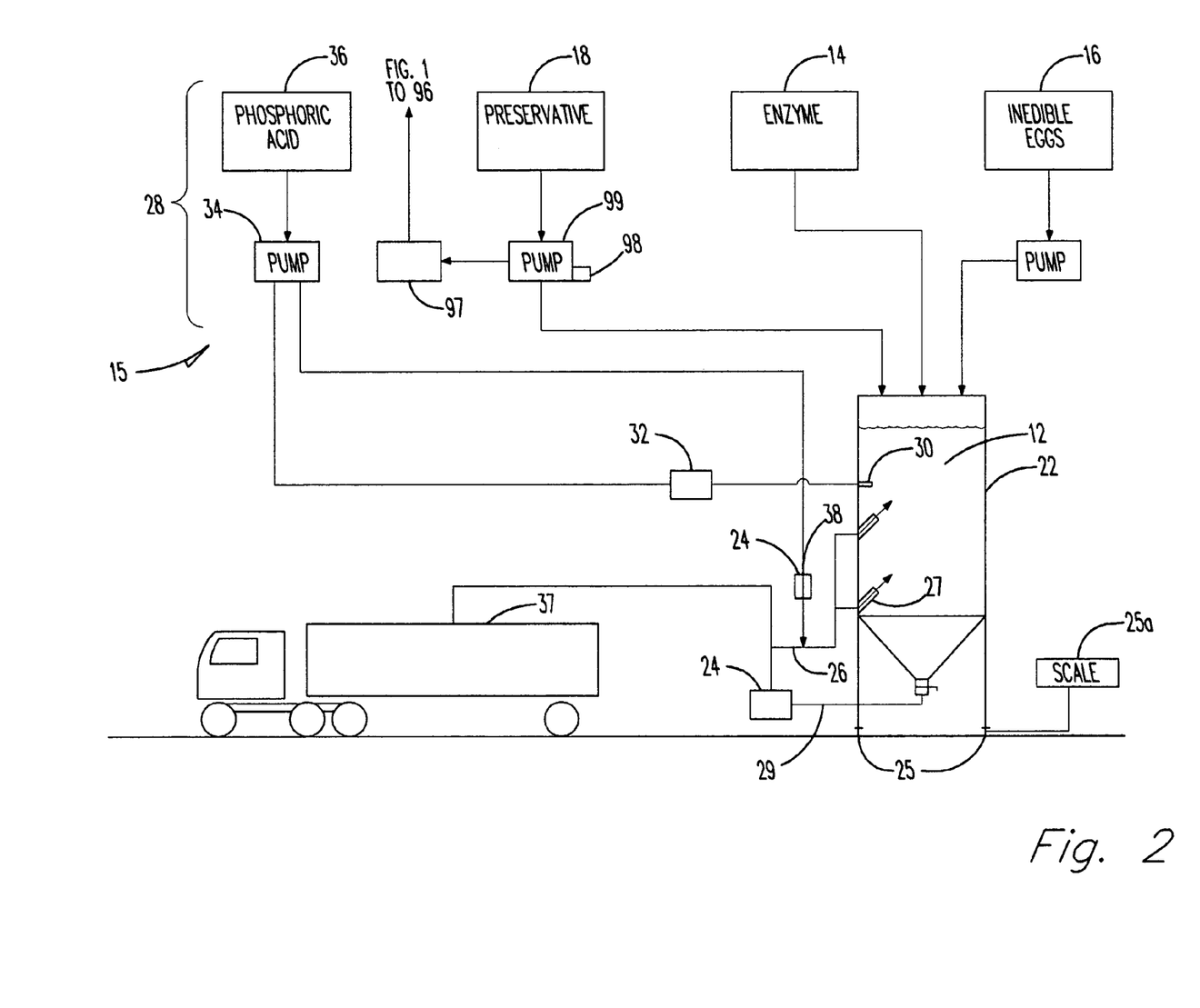
FIG. 2 is a diagram showing the enzymatic digest mixing assembly portion of the present invention.
Figure 3:
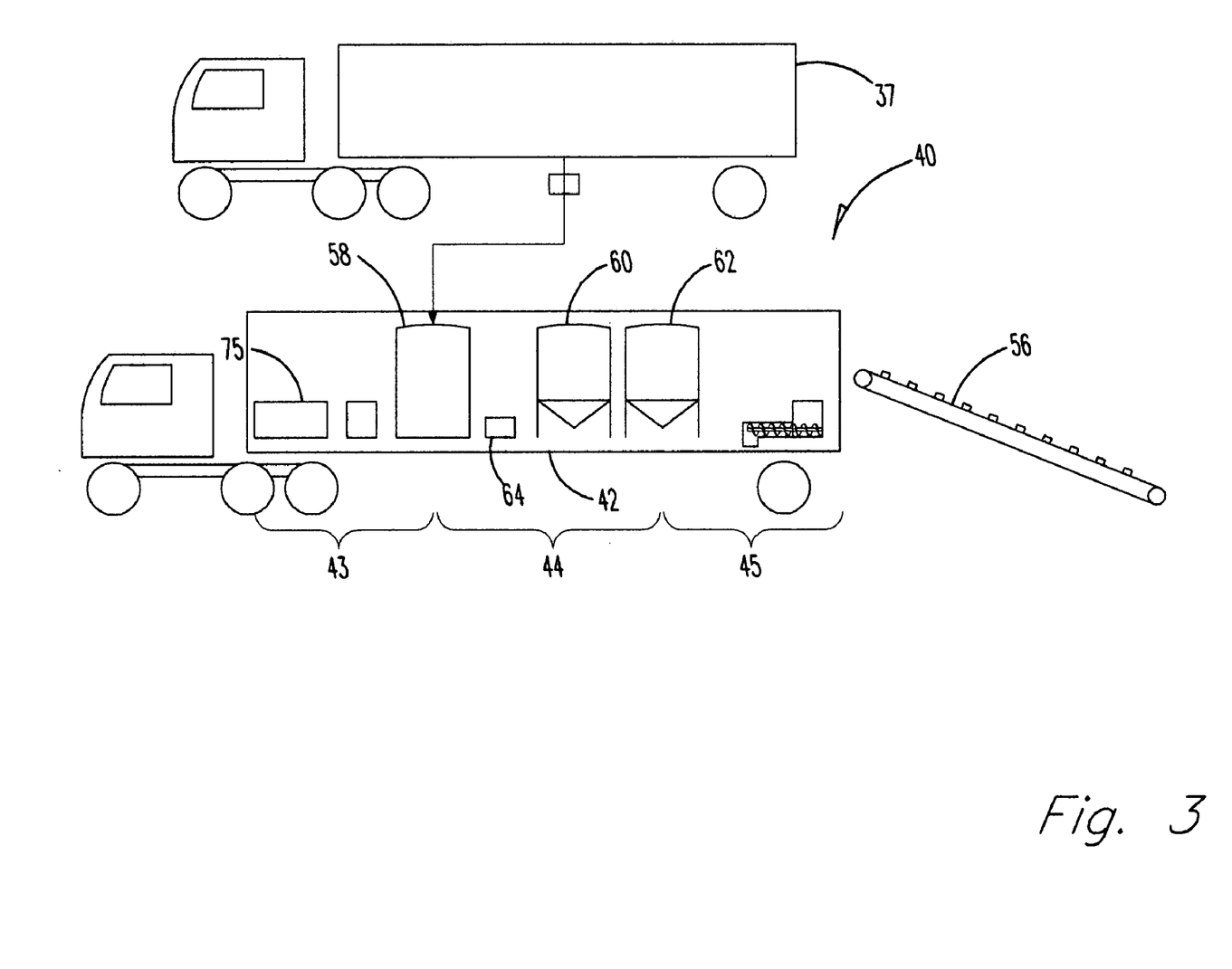
FIG. 3 is a side view of the mobile grinding assembly portion of the present invention.
Figure 4:
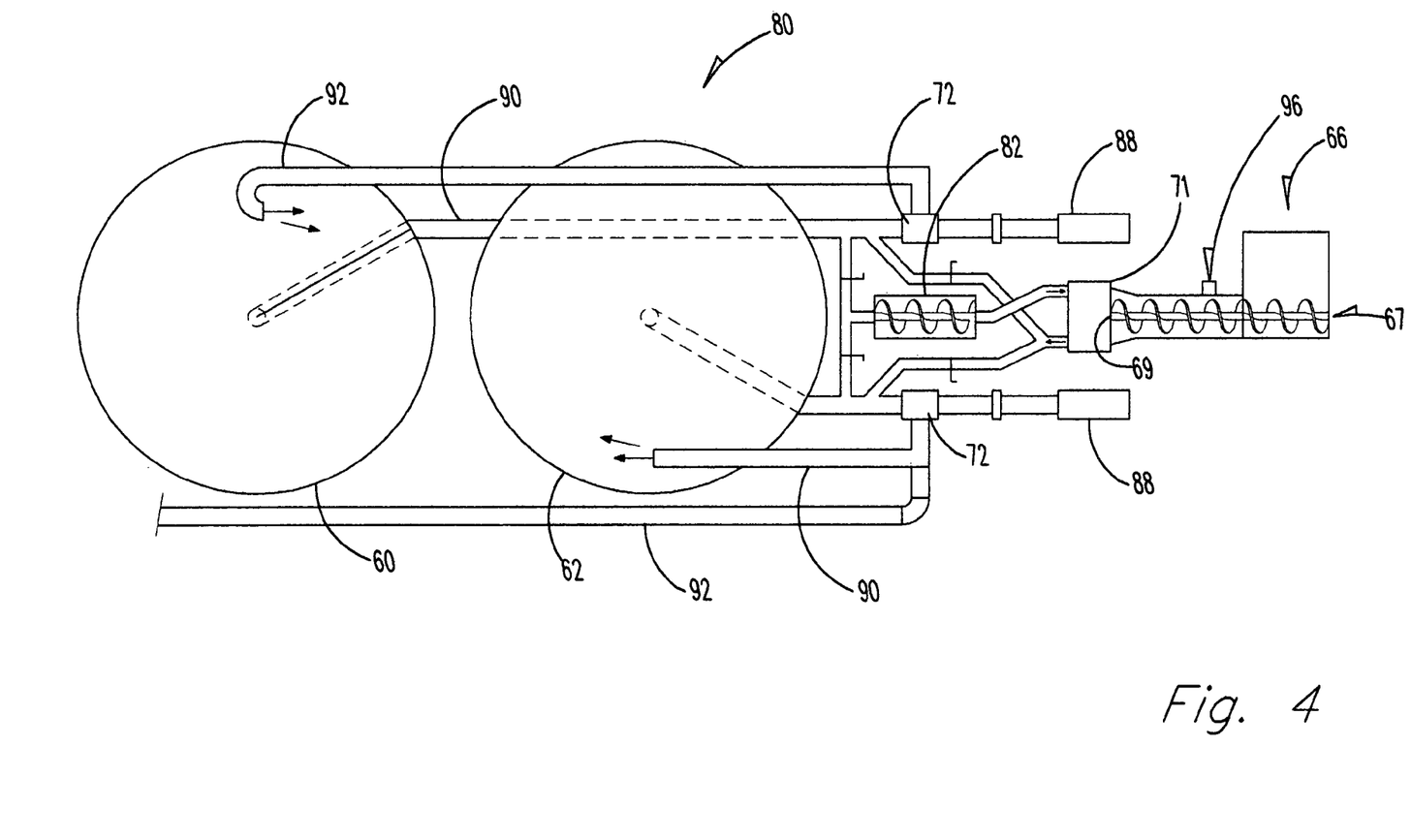
FIG. 4 is an enlarged plan view of the mobile grinding assembly of FIG. 3.
Figure 5:
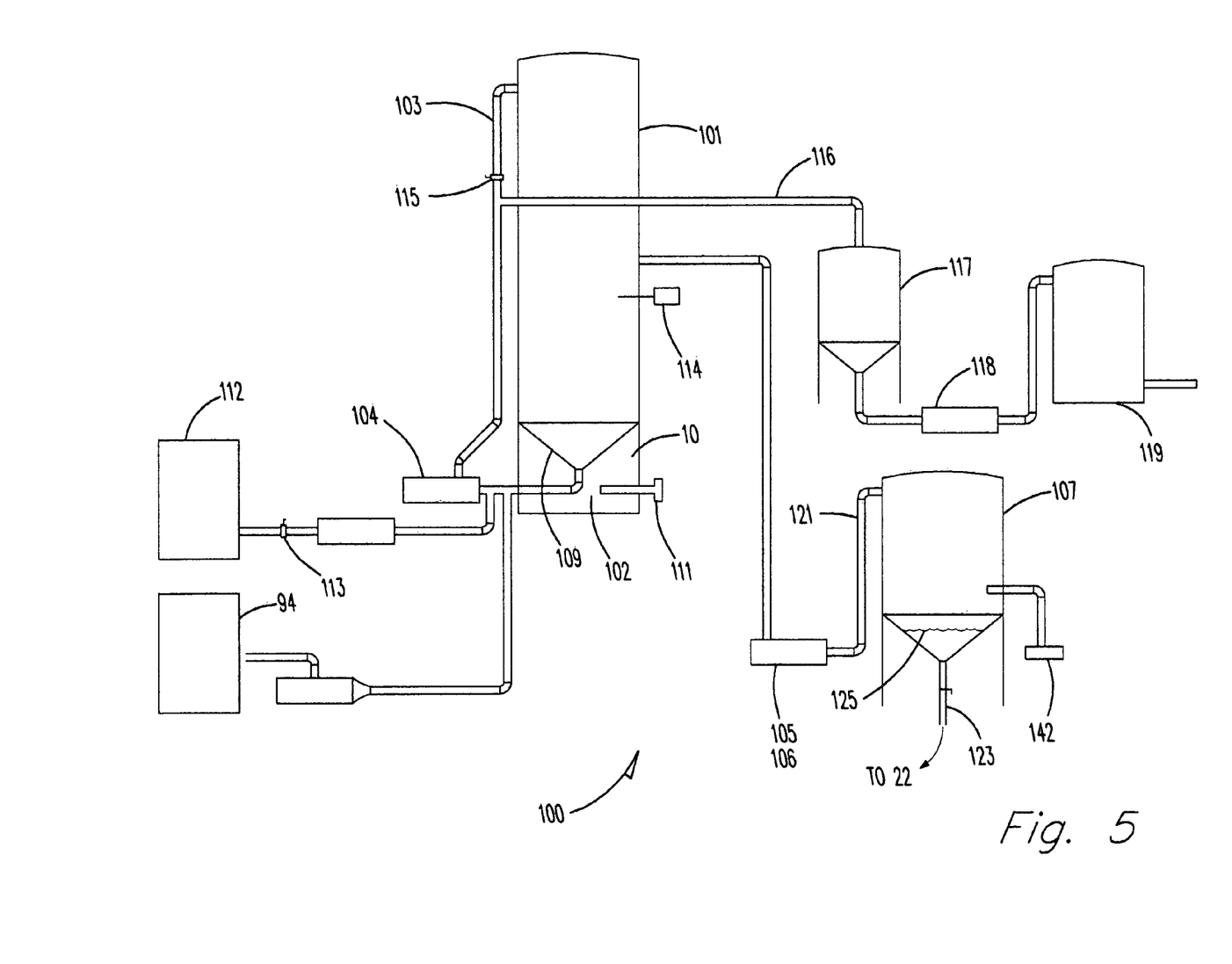
FIG. 5 is a side view of the digesting and emulsifying assembly portion of the present invention.
Figure 6:
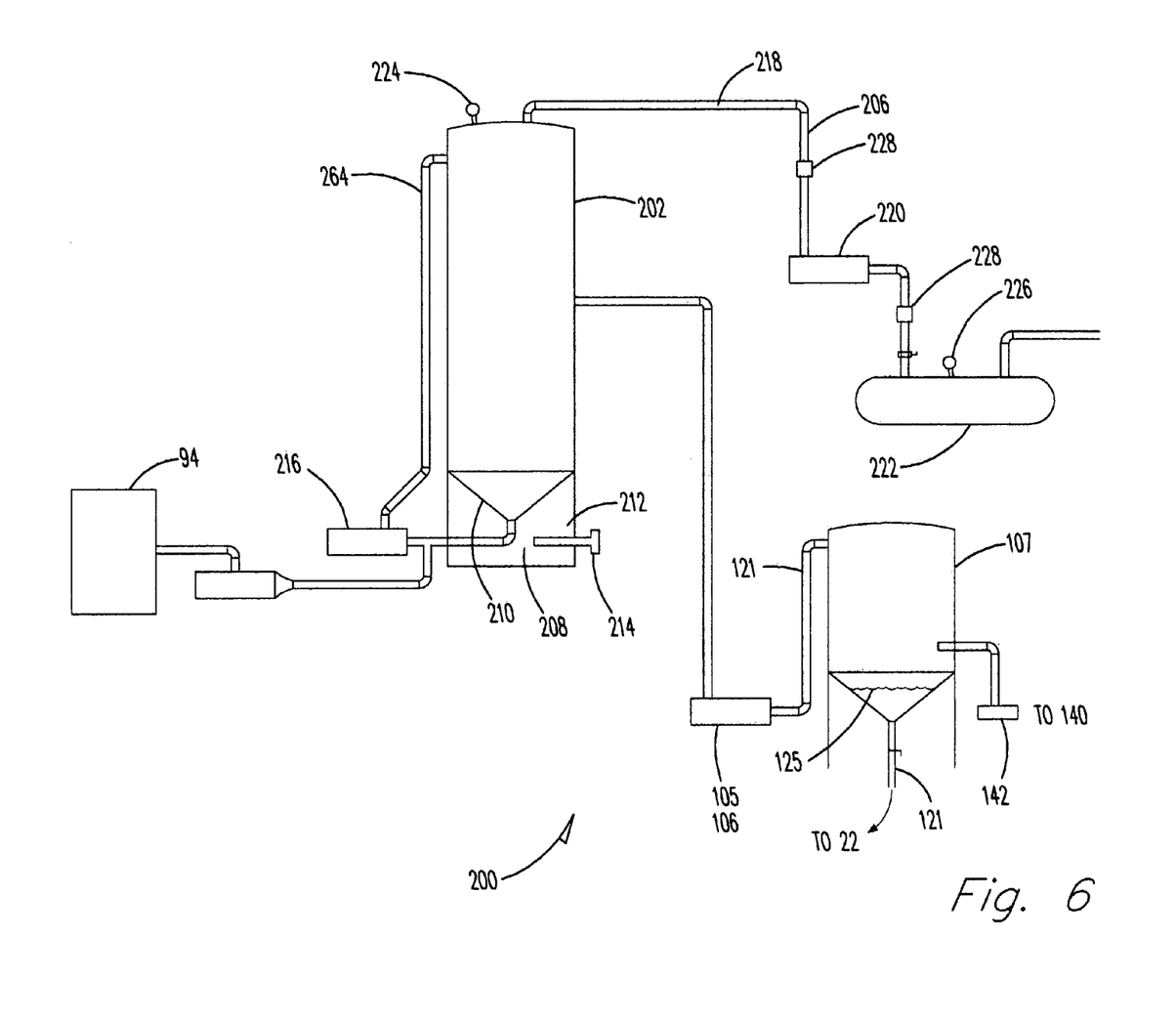
FIG. 6 is a side view of the fermentation assembly portion of a second embodiment of the present invention.
Figure 7:
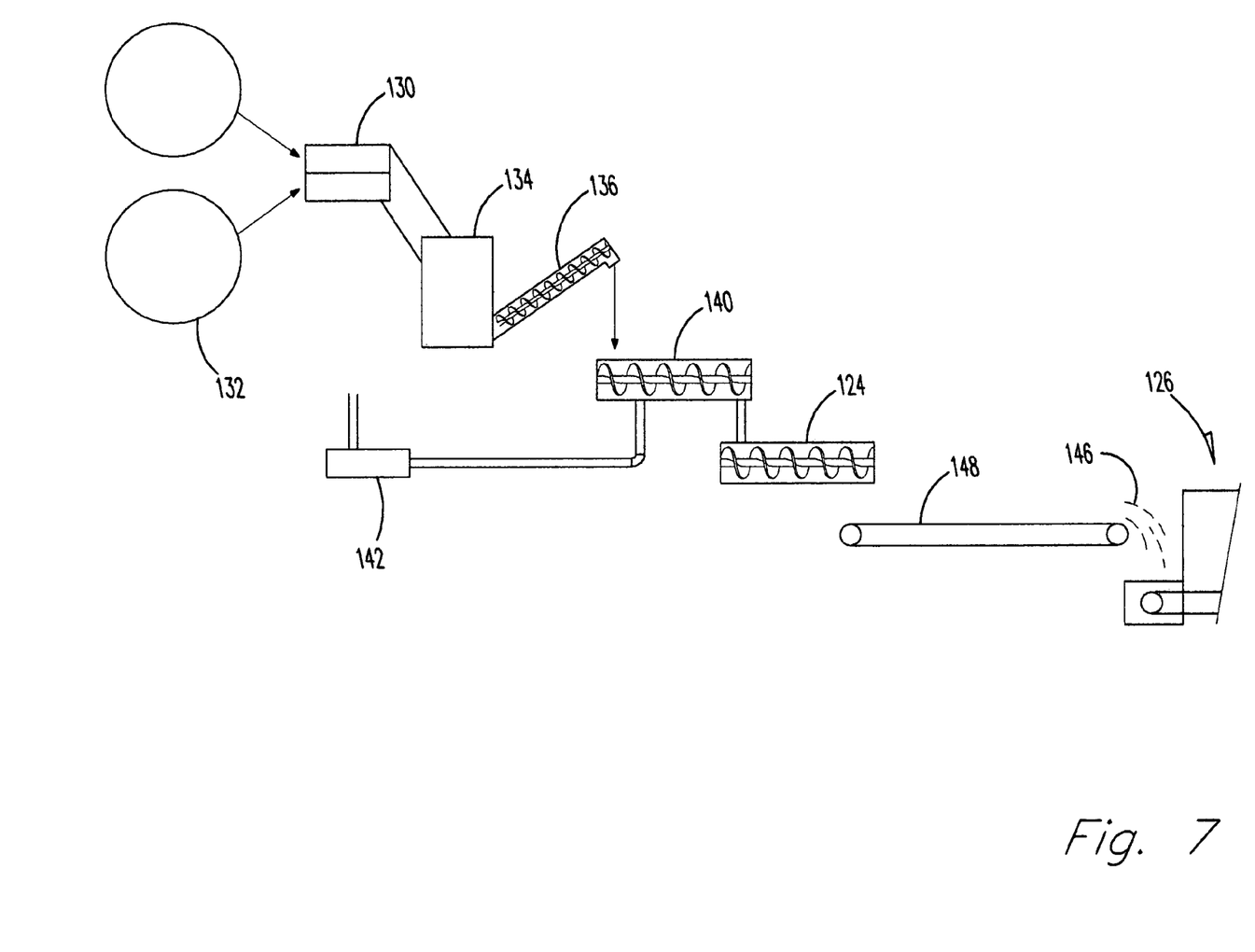
FIG. 7 is a block diagram showing the components of the dough mixing apparatus and extruder of the drying system portion of the present invention.
Figure 8:
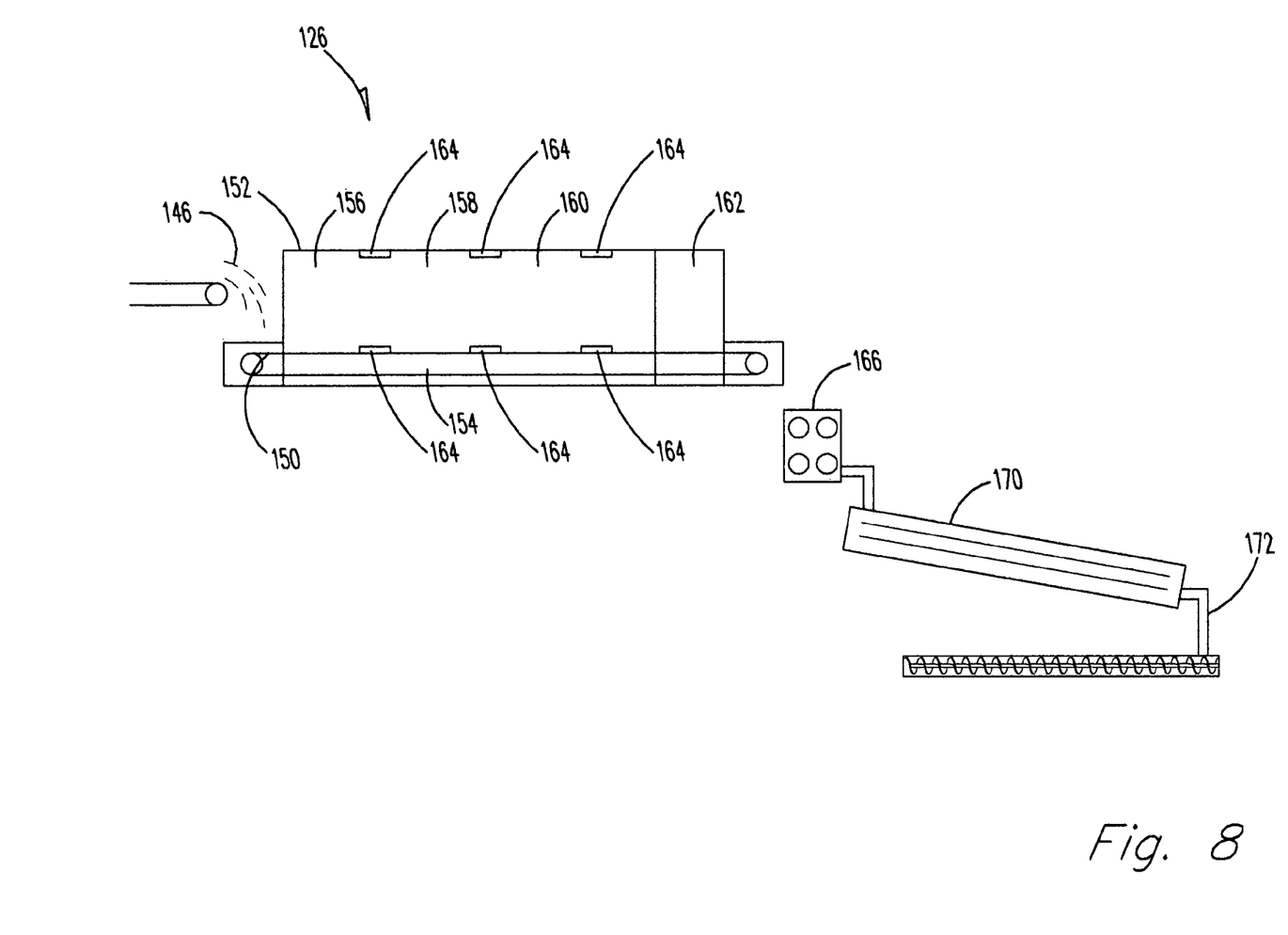
FIG. 8 is a block diagram of the drying apparatus of the drying system portion of the present invention.

The apparatus and process for naturally recycling protein waste of the present invention comprises an enzymatic digest mixing assembly shown generally as 15 in FIG. 2, a mobile grinding assembly shown generally as 40 in FIGS. 3 and 4, a digesting and emulsifying assembly shown generally as 100 in FIG. 5 or a fermentation assembly shown generally as 200 in FIG. 6, and a drying system shown generally as 126 in FIGS. 7 and 8.

Figure 9:
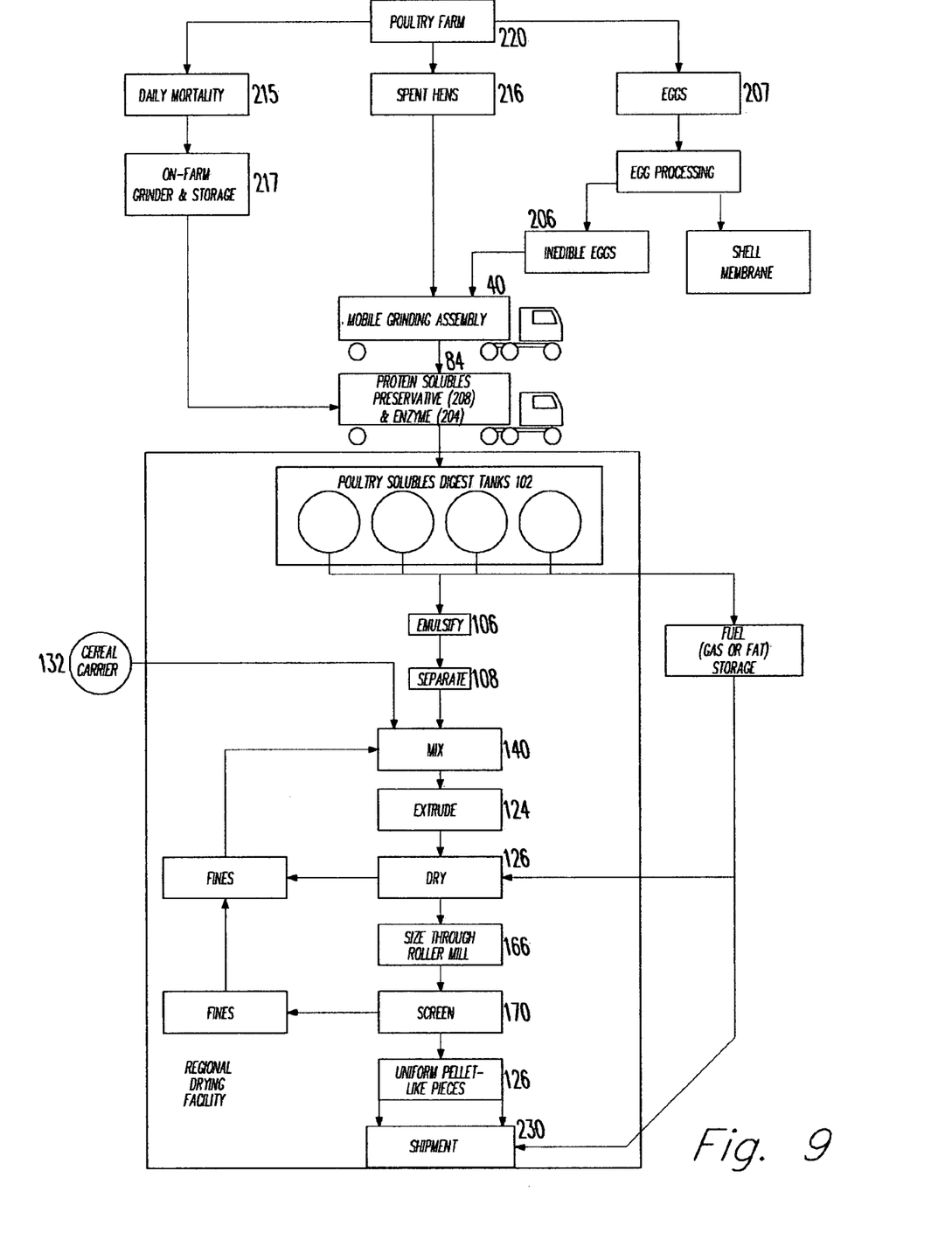
FIG. 9 is a flow diagram showing the steps for the process for natural recycling of protein waste of the present invention.

In general, the process is shown in the flow chart depicted in FIGS. 2 and 9 and requires that an enzymatic digest medium 12 of a particular pH level be prepared and stored until such time as it is needed. The medium 12 of the preferred embodiment comprises enzymes 14, inedible egg 16, a preservative 18 and water. The enzymes 14 may include protease to break down and digest most proteins, and keritinase to aid in digestion of feathers, The preservative 18 restricts multiplication of bacteria or microorganisms which could adversely affect the end product. An example of one such preservative 18 is sodium meta-bisulfite. Although inedible egg is a logical choice when the apparatus is used in conjunction with poultry production, other fluid wastes such as outdated ice cream, molasses, milk by products, and others that include proteins, fat, and water could be appropriately substituted.

In the preferred embodiment, the pH is adjusted by measured addition of phosphoric acid to maintain an optimal level of pH 5 or within the range of about 4-6. Using phosphoric acid to effect a change in pH also adds phosphorous to the medium and, in turn, provides a high phosphorous product which may enhance the desirability of the additive for animal feed. Other acidic solutions may also be used. For example, lactic acid is one such reasonable alternative. In the case where lactic acid is used, the fermentation process which occurs as a natural consequence of the use of lactic acid, (in addition to digestion by enzymes) also acts to break down the protein waste and lowers the pH at the same time.

Protein waste which may be in the form of spent hens 216 is then ground and the enzymatic digest medium 12 and ground protein waste 216 are thoroughly mixed and re-circulated through a chopper pump 88 to produce a protein solubles mixture 84. The protein solubles mixture 84 is maintained at or heated to a temperature optimal for enzyme digestive action which ranges between about 90 degrees Fahrenheit and 110 degrees Fahrenheit and recirculated periodically until the mixture is mostly liquid. The heat created by the exothermic digestive process and the friction of recirculation in certain conditions may be enough to maintain the optimal temperature and, if not, additional heat can be provided. The preferred method suggests recirculating the mixture for 1 hour every 12 hours for 3-4 days, however, the speed of the process may be increased if additional enzyme is used. When the protein solubles mixture 84 can be strained and the number of quills remaining in the strainer is acceptable, the digestion is complete. The protein solubles mixture 84 is then emulsified to disperse fats and proteins and allowed to separate. The resulting water layer 114 is drained off and recycled to be re-used for mixing enzymatic digest medium 12 and, after draining the water layer 114 several times, the emulsified proteins 121 is mixed with a carrier 132.

The carrier 132 is delivered to a high speed mixer 140 by volumetric feeder 130 and comprises a relatively high surface area to volume ratio which acts to absorb some of the moisture. Upon mixing with the emulsified proteins 121, a doughlike mixture is produced. The doughlike mixture is then extruded into a plurality of pellet-like pieces 146 and the pellet-like pieces are passed through a drying apparatus 126 which uses air flow, multiple heat zones, and at least one cooling zone for further removal of moisture. The pellet-like pieces are finally sized through a mill 166 to a uniform, granular size. In the preferred embodiment the mill 166 is a hammer mill. The off-size pellet-like pieces are removed and the remaining uniform, granular pellet-like pieces can be packaged. The apparatus used to accomplish the foregoing process is described below.

The enzymatic digest mixing assembly 15 shown best in FIG. 2 is used to mix enzymes 14, inedible egg 16, and a preservative 18 with water to form an enzymatic digest medium 12 of an optimal pH level and comprises at least one enzymatic digest mixing tank 22, pumping means 24, a re-circulating assembly 26 and means for adjusting the pH level of the medium which, in the preferred embodiment, is a pH adjustment assembly 28. The pumping means 24 of the preferred embodiment comprises a first centrifugal pump and the re-circulating assembly 26 comprises a first inductor nozzle 27 associated with the pumping means 24 and a return pipe 29 for circulating the enzymatic digest medium 12. The preferred embodiment includes load cells 25 associated with a digital scale 25a and positioned such that addition of the enzymes, preservatives, inedible egg can be measured. It is also contemplated that, in addition to external measuring of the ingredients, other internal measurement options such as ultrasound and light beams may be used to monitor the amounts of each ingredient as it is added.

The pH adjustment assembly 28 of the preferred embodiment comprises a pH probe 30, a pH monitor 32, and a first positive displacement pump 34 all electrically associated, and a supply of acidic solution 36 fluidly connected to the positive displacement pump 34 and to the mixing tank 22 through a check valve 38. The first positive displacement pump 34 of the preferred embodiment includes a variable speed motor, preferably pumping 1-10 gallons per minute. Once the enzymatic digest medium 12 is placed in the mixing tank 22 and recirculated for at least 3-5 minute, the pH probe 30 provides pH level to the pH monitor 32. The pH monitor 32 compares the pH level 31 with an optimal level and sends a signal to the positive displacement pump 34 to move the acidic solution 36 into the mixing tank 22 where recirculation continues. The re-circulating assembly 26 continues to mix the enzymatic digest medium 12 and the pH probe 30 again measures the pH level, the monitor 32 compares the level to the optimal level, and again determines whether acidic solution 36 should be added to the mixing tank 22. When the pH level reaches the optimal level, the enzymatic digest 18 is ready to be used or stored.

The enzymatic digest medium 12 of the preferred embodiment includes, per ton, about 2½ pounds of protease and keritinase 204, about 2 pounds of preservative 18, and the remaining pounds inedible egg 16 and water. The pH is lowered to about 5 by addition of phosphoric acid 36. This pH level is optimal for this particular enzymatic digest medium, however a range from about 4-6 may be effective and the amount of enzyme may be altered according to the speed of digestion desired and the enzymes used.

Once the enzymatic digest medium 12 has been prepared, it can either be stored or it can be moved via tanker truck 37 to the mobile grinding assembly 40 where it will be mixed with ground protein waste 216. Referring now to FIGS. 3 and 4, the mobile grinding assembly 40 comprises a movable platform 42 which, in the preferred embodiment, is a semi trailer, and includes a front portion 43, a mid portion 44 and a rear portion 45, a conveyor belt 56 for moving protein waste, a holding tank 58 in which the enzymatic digest 18 is stored, at least one prep tank 60, 62, and a pump 64 to move the enzymatic digest medium 12 from the holding tank 58 to the at least one prep tank 60, 62. The mobile grinding assembly 40 further comprises grinding means 66 which, in the preferred embodiment, comprises a grinder inlet 67 positioned near the conveyor belt 56, a grinder plate 68, and a grinder outlet 69 and at least one grinder knife 70 wherein the grinder outlet 69 is positioned such that output from the grinder outlet 69 may flow by closed connection 71 into a hydro pump 82 the hydro pump 82 having a lower outlet 74. A specific example of grinding means 66 is a Weiler Meat Grinder utilizing a 7/16" plate. However, different plate combinations can be used such as double-cut, double-knife combinations with a ¾" or ⅜" plate. In this situation, one knife is positioned on the inside of the grinder plate 68 and another on the outside of the grinder plate 68.

The grinding assembly 40 further comprises mixing means 80 which, in the preferred embodiment, comprises at least one second positive displacement pump 72, which is fluidly connected to the at least one prep tank 60, 62 and to the hydro pump 82 of the grinding means 66 such that the enzymatic digest medium 12 can be moved to the hydro pump 82 where output from the grinder outlet 69 is mixed with the enzymatic digest medium 12 to form a protein solubles mixture 84. The enzymatic digest medium 12 is pumped against the grinder outlet 69 and washes ground protein waste down into the hydro pump 82. The lower outlet 74 of the hydro pump 82 is fluidly connected to a centrifugal chopper pump 88 which is further associated with the at least one prep tank 60 or 62 and a recirculation piping system 92 including an inductor nozzle 90. This arrangement provides a way to move the protein solubles mixture 84 through the chopper pump 88 and into the prep tank 60 via the inductor nozzle 90 which is positioned to generate a circular flow in the prep tank 60. The mixture 84 is continually recirculated through the chopper pump 88 until it is of desired consistency and thoroughly mixed. This usually requires several minutes.

The protein solubles mixture 84 is then transported to the digesting and emulsifying assembly 100 shown in FIG. 5 either via pumping it directly or by pumping it first to a tanker truck 94 and then to the assembly 100. The mobile grinding assembly 40 is a closed system wherein the grinder inlet 67 is the only input open to the environment.

Where more than one prep tank 60, 62 is present, one prep tank 60 may be recirculated or unloaded while another is being filled and recirculated. In this embodiment, a separate chopper pump is associated with each prep tank.

In one embodiment, the front portion 43 of the movable platform 42 is occupied by a power source 75 in the form of a generator, the mid portion 44 of the movable platform 42 accommodates the holding tank 58 and prep tanks 60, 62, and the rear portion 45 includes the grinding means 66 and the conveyor belt 56. The at least one prep tank 60, 62 of the preferred embodiment is a cone-bottomed tank.

The apparatus of the preferred embodiment further includes an electronic load sensor 96, a programmable logical computer circuit 97, and a variable frequency drive 98, and a preservative pump 99 to delivery preservative 18 to the enzymatic digest medium 12. The load sensor is located on the grinding means that senses a load of the grinding means. The variable frequency drive 98 controls the preservatives pump 99. The load sensor and variable speed drive are connected to the circuit 97. The circuit 97 is programmed with a program to determine the amount of preservative to pump based on a load. In the preferred embodiment, a relationship is established between the amperage load on the grinding means 66 and the desired revolutions per minute to run the preservatives pump 99. The following program is used in the preferred embodiment:

| Grinder Amp | Load | Preservative Pump Rpm |
| --- | --- | --- |
| 40 amps | no load | 0 RPM |
| 50 amps | 25% load | 437 RPM |
| 60 amps | 50% load | 875 RPM |
| 70 amps | 75% load | 1300 RPM |
| 80 amps | Full load | 1800 RPM |

The digesting and emulsifying assembly 100 of the preferred embodiment is stationary rather than mobile. The digesting and emulsifying assembly 100 comprises a digester tank 101 for digesting the protein solubles mixture 84, means for heating the mixture 102, means for recirculating the mixture 103 including a centrifugal pump 104 for periodic mixing, means for collecting fats from the digester tank 107, and an emulsifier 105. The emulsifier 105 is fluidly connected to a pump 106, the digester tank 101, and a separator tank 108.

In the preferred embodiment, the digester tank 101 is a non-pressure tank with a cone bottom 109 enclosed within a housing 110. The heating means 102 of the preferred embodiment is a heating element 111 and water (not shown) enclosed in the housing 110. The housing 110 of the preferred embodiment is a vented water jacket. The heating element 111 of the preferred embodiment heats the water in the housing to about 120° F. and in turn warms the protein solubles mixture 84 from about 90° F. to about 110° F. The protein solubles mixtures 84 is recirculated while it digests. In certain conditions friction from circulation and the exothermic digestion may provide heat sufficient to maintain the digest medium at optimal temperature and reduce or negate the need for additional heat.

The fat collection means 107 of the preferred embodiment includes an acid storage tank 112, a positive displacement pump 113, the centrifugal pump 104, a first fats storage tank 117, a centrifuge 118, and a second fats storage tank 119. After digestion of the protein solubles mixture 84 in the digest tank 101, the fat (not shown) is separated from the protein solubles 84 by recirculating the protein solubles 84 with acid (not shown). In the preferred embodiment, acid is stored in the acid storage tank 112 and pumped into recirculation means 103 by the positive displacement pump 113 while the protein solubles 84 are recirculated. Alternatively, the acid could be pumped solely by the centrifugal pump 104. A pH probe 114 in the digest tank 101 controls the pump 113 and centrifugal pump 104 to stop the pumps at a desired pH level.

Because of the introduction of acid and the corresponding drop in pH level, fat (not shown) will settle out of the digest tank 101. The settled fat is pumped out of the digester tank 101 using the centrifugal pump 104. The recirculation means 103 includes a recirculation valve 115 and a closable connection 116 connecting the digest tank 101 to the first fat storage tank 117. During recirculation, the recirculation valve 115 is open and the closeable connection 115 is closed. During collection of fat the recirculation valve 115 is closed and the closeable connection 116 is open. In the preferred embodiment the centrifugal pump 104 stops pumping fat when all of the fat in the digester tank 101 has been removed as confirmed by visual operation.

The centrifuge 118 is fluidly connected to the first storage tank 117 and the second fat storage tank 119. The centrifuge 118 acts to pump the fat from the first storage tank 117 and separate water from fat. The separated water (not shown) can be recirculated back into the protein solubles mixture 84 and water is so recycled in the preferred embodiment. Separated fats are stored in the second storage tank 119. The stored fats can be used as a fuel source for the drying system 120 or for other purposes.

After digestion and removal of fat, the protein soluble mixture 84 is pumped into the emulsifier 105 for further removal of fats. Emulsification produces emulsified proteins 121 which are transferred to a separator tank 108. An example of an emulsifier suitable for this purpose is Mincemaster Dual Plate. The separator tank 108 has a closeable opening 123 in fluid connection with the enzymatic digest mixing tank 22. A water layer 123 that forms in the separator tank 108 can be drained for use in mixing additional digest medium 12.

Referring to FIGS. 7 and 8, the emulsified proteins 121 are moved to the drying system 120 which comprises a dough mixing apparatus 122, an extruder 124 and a drying apparatus 126. The dough mixing apparatus 122 of the preferred embodiment shown in FIG. 6 comprises a volumetric feeder 130 for measuring an absorbing carrier 132 to be mixed with the emulsified proteins 121 and which is positioned over a mill 134 for finely grinding the absorbing carrier 132. The mill 134 of the preferred embodiment is a high speed hammer mill or disc mill. A second conveyor belt 136 moves the absorbing carrier 132 from the mill 134 to a high speed continuous mixer 140. A third positive displacement pump 142 is associated with the separator tank 108 and moves the emulsified proteins 121 to the high speed mixer 140 where it is mixed with the absorbing carrier 132 to produce a dough-like mixture. In the preferred embodiment, the absorbing carrier 132 is a substance with characteristics like wheat mids, soybean meal, corn, or a previously dried material made for such purpose and the third positive displacement pump is of the variable speed variety.

The doughlike mixture is moved to the extruder 124 which pressure-forces moisture out and produces a plurality of pellet-like pieces 146. In the preferred embodiment the pellet-like pieces are 3/16" and of random length. The pellet-like pieces 146 are extruded onto an oscillating belt 148 which distributes the pellet-like pieces 146 evenly and connects the extruder 124 to the drying apparatus 126. Additional moisture is removed by the drying apparatus 126 using heat and air movement. The drying apparatus 126 shown best in FIG. 8 comprises a dryer bed 150 positioned to receive the pellet-like pieces 146 from the oscillating belt 148, a housing 152 through which a dryer bed conveyor belt 154 moves and conveys the pellet-like pieces 146 and which includes at least one heating zone 156, 158, 160, at least one cooling zone 162, and means to direct airflow 164. The mill 166 receives the pellet-like pieces 146 after they emerge from the housing 152 and sizes the plurality of pellet-like pieces 146 to a uniform size. A vibrating screen 170 is used to remove any of the plurality of the pellet-like pieces 146 which are of a non-uniform size. Means to direct airflow 164 may comprise fans positioned to alternate the flow of air to provide uniformity in drying. In the preferred embodiment, the heat zones 156, 158, 160 provide temperatures of 300, 275, and 250 Fahrenheit, in this order, such that the maximum temperature of the plurality of pellet-like pieces does not exceed 250. If the heat of the pellet-like pieces 146 exceeds this level their taste can be too bitter and the amino acids can be degraded. The cool zone 162 returns the pellet-like pieces 146 to within 10 degrees of ambient temperature. Vents 171 return the heated air from the cool zone 162 to the heat zones.

The protein solubles mixture 84 can alternatively be digested through fermentation. In this second preferred embodiment, the pH of the enzymatic digest medium 12 is adjusted using lactic acid. The fermentation itself replaces the enzymatic digest and a fermentation assembly 200 replaces the digest and emulsification assembly 100. The fermentation assembly includes a non-vented low pressure tank 202, means for recirculating protein solubles 204, and means for collecting gas 206.

The fermentation tank 202 has means for heating the mixture 208 comprising a cone bottom 210 surrounded by a housing 212 filled with water (not shown) and heated by a heating element 214. The heated water in turn heats the protein solubles mixture 84 and microorganisms (not shown) within the tank 202. The microorganisms in the tank 202 is preferably bacteria that produce methane gas. Recirculation means 304 of the second preferred embodiment include a centrifugal pump 216 that recirculates the contents of the tank 202. In the second embodiment, gas collection means 206 comprises piping 218 in fluid connection with the tank 202, a compressor 220, and a pressure tank 222. During recirculation, the bacteria produce gas (not shown) and increase pressure in the tank 202. The second preferred embodiment of the tank 202 includes a pressure sensor 224 to monitor pressure in the tank 202. At the appropriate pressure, the pressure sensor 224 activates the compressor 220 which compresses the gas for storage in the pressure tank 222. As a safety measure, the pressure tank 222 of the preferred embodiment includes a pressure gauge 228. To prevent backflow of gas, the piping 218 includes check valves 228 located before and after the compressor 220. The stored methane gas can be used as a fuel source for the dryer system 120 or for other purposes. After digestion and collection of gas, the protein soluble mixture 84 of the second preferred embodiment is pumped into the emulsifier 105 for further removal of fats consistent with the preferred embodiment of the digest and emulsification assembly 100.

Thus, the present invention has been described in an illustrative manner. It is to be understood that the terminology that has been used is intended to be in the nature of words of description rather than of limitation.

Many modifications and variations of the present invention are possible in light of the above teachings. For example, it may be possible for all parts of the system to be made in mobile form or for none of the system to be mobile. Many different pumps are available and may be used according to need. The enzymatic digest medium can be altered to accommodate different protein/bone/feather combinations. Therefore, within the scope of the appended claims, the inventor so defines his invention:

We claim:

1. An apparatus for recycling of protein waste comprising:
   a) an enzymatic digest mixing assembly for mixing a medium and for adjusting its pH level;
   b) a mobile grinding assembly mounted on a movable platform and comprising grinding means for protein waste and mixing means for combining said ground protein waste and said enzymatic digest medium to produce a protein solubles mixture;
   c) a digesting and emulsifying assembly;
   d) a drying system comprising a dough mixing apparatus, an extruder, and a drying apparatus;
   e) said mobile grinding assembly further comprises:
      i) said movable platform having a front portion and a mid portion and a rear portion with a conveyor belt for transporting said protein waste mounted on said rear portion;
      ii) a housing mounted on said movable platform;
      iii) said housing encloses a power source, a holding tank for said enzymatic digest medium, at least one cone bottomed prep tank, and a pump to move said enzymatic digest medium from said holding tank to said at least one cone bottomed prep tank;
      iv) said grinding means comprises a grinder inlet positioned near said conveyor belt, a grinder plate, and a grinder outlet positioned to flow into a hydro pump with a lower outlet;
      v) said mixing means comprises a first positive displacement pump fluidly connected to said at least one cone bottomed prep tank and said hydro pump to move said enzymatic digest medium to said hydro pump wherein said lower outlet of said hydro pump is fluidly connected to a centrifugal chopper pump associated with said cone bottomed prep tank and with a re-circulation piping system and inductor nozzle such that said enzymatic digest medium and said ground protein waste can be mixed and continually re-circulated in said cone bottomed prep tank to form a protein solubles mixture.

2. The recycling apparatus of claim 1 wherein said digesting and emulsifying assembly comprises:
   a) a digester tank;
   b) means for heating said protein solubles mixture in said digester tank;
   c) means for recirculating said protein solubles mixture in said digester tank;
   d) means for collecting fat from said protein solubles mixture in said digester tank; and
   e) an emulsifier in fluid connection with said digester tank for emulsifying said protein solubles mixture to produce emulsified proteins.

3. The recycling apparatus of claim 2 wherein said digester tank includes a cone bottom and said heating means comprises:
   a) a housing surrounding said cone bottom;
   b) water within said housing; and
   c) a heating element within said housing for heating said water.

4. The recycling apparatus of claim 2 wherein said recirculation means comprises a centrifugal pump in fluid connection with said digester tank and said cone bottom.

5. The recycling apparatus of claim 2 wherein said fat collection means comprises:
   a) an acid storage tank in fluid connection with said recirculation means;
   b) a first fat storage tank in fluid connection with said digester tank;
   c) a centrifuge in fluid connection with said first fat storage tank for removing water from fats collected from said digester tank; and
   d) a second fat storage tank in fluid connection with said centrifuge.

6. The recycling apparatus of claim 5 wherein said fat collection means further comprises a valve located on said recirculation means and a closeable connection connecting said recirculation means and said first fats storage tank.

7. The recycling apparatus of claim 5 wherein said fat collection means further comprises a positive displacement pump in fluid connection with said acid tank and said recirculation means for pumping acid into said recirculation means.

8. The recycling apparatus of claim 2 wherein said digest and emulsification assembly further comprises a separator tank having a closeable opening fluidly associated with said enzymatic digest mixing assembly to allowing a water layer to be drained from said separator tank and recycled for use in said means for mixing an enzymatic digest medium.

9. The recycling apparatus of claim 2 wherein said fat collected is supplied to said drying system for use as fuel to power said drying system.

10. The recycling apparatus of claim 1 wherein said digesting and emulsifying assembly is a fermentation assembly comprising:
    a) a fermentation tank;
    b) microorganisms located within said digester tank;
    c) means for heating said protein solubles mixture and microorganisms in said digester tank;
    d) means for recirculating said protein solubles mixture and microorganisms in said digester tank;
    e) means for collecting gas from said digester tank; and
    f) an emulsifier in fluid connection with said digester tank for emulsifying said protein solubles mixture to produce emulsified proteins.

11. The recycling apparatus of claim 10 wherein said digester tank includes a cone bottom and said heating means comprises:
    a) a housing surrounding said cone bottom;
    b) water within said housing; and
    c) a heating element within said housing for heating said water.

12. The recycling apparatus of claim 10 wherein said recirculation means comprises a centrifugal pump in fluid connection with said digester tank and said cone bottom.

13. The recycling apparatus of claim 10 wherein said gas collection means comprises:
    a) a pressure tank;
    b) a compressor for compressing said gas into said pressure tank;
    c) piping fluidly connecting said fermentation tank, said compressor, and said pressure tank; and
    d) a pressure sensor located on said tank to monitor pressure inside said fermentation tank and activate said compressor at an appropriate pressure.

14. The recycling apparatus of claim 13 wherein said gas collection means further comprises check valves located on said piping between said fermentation tank and said compressor and between said compressor and said pressure tank.

15. The recycling apparatus of claim 13 wherein said gas collection means further comprises a pressure gauge located on said pressure tank.

16. The recycling apparatus of claim 10 wherein said fermentation assembly further comprises:
    a) a separator tank;
    b) a pump in fluid connection with said digester and said separator tank
    c) said separator tank having a closeable opening fluidly associated with said enzymatic digest mixing assembly to allowing a water layer to be drained from said separator tank and recycled for use in said means for mixing an enzymatic digest medium.

17. The recycling apparatus of claim 10 wherein said gas collected is supplied to said drying system for use as fuel to power said drying system.

18. The recycling apparatus of claim 1 wherein said enzymatic digest mixing assembly comprises at least one mixing tank, pumping means, a re-circulating assembly, and a pH adjustment assembly.

19. The recycling apparatus of claim 18 wherein said pumping means comprises a first centrifugal pump.

20. The recycling apparatus of claim 19 wherein said re-circulating assembly comprises a first inductor nozzle associated with said centrifugal pump and a return pipe for circulating the enzymatic digest medium.

21. The recycling apparatus of claim 20 wherein said pH adjustment assembly comprises:
    a) a pH probe internal to said mixing tank;
    b) a pH monitor associated with said pH probe;
    c) a second positive displacement pump; and
    d) a supply of acidic solution fluidly connected to said first positive displacement pump and to said mixing tank through a check valve wherein said pH probe provides a pH level of said enzymatic digest medium to said monitor and said monitor compares said pH level to a pH between about 4 and about 6 and signals said first positive displacement pump to pump said acidic solution to said mixing tank until said optimal pH level is reached.

22. The recycling apparatus of claim 21 wherein said acidic solution includes an acid selected from the group consisting of phosphoric acid and lactic acid.

23. The recycling apparatus of claim 1 wherein said dough mixing apparatus comprises:
    a) a volumetric feeder to deliver an absorbing carrier positioned over a mill for grinding said absorbing carrier;
    b) a high speed continuous mixer;
    c) a second conveyor belt to move said absorbing carrier from said feeder to said high speed continuous mixer;
    d) a third positive displacement pump associated with said separator tank for moving emulsified protein solubles to said high speed mixer for producing a doughlike mixture.

24. The recycling apparatus of claim 1 wherein said extruder pressure forces moisture out and produces a plurality of pellet-like pieces and an oscillating belt connects said extruder to said drying apparatus.

25. The recycling apparatus of claim 24 wherein said drying apparatus comprises:
   a) a dryer bed positioned to receive said dough pellet-like pieces from said oscillating belt;
   b) a housing through which a dryer bed conveyor belt moves;
   c) said housing having at least one heating zone, at least one cooling zone, and means for direct airflow to dehydrate said pellet-like pieces;
   d) a hammer mill for sizing said plurality of pellet-like pieces to uniform size; and
   e) a vibrating screen to remove any said pellet-like pieces of non-uniform size.

26. The recycling apparatus of claim 1 wherein said apparatus further includes:
   a) an electronic load sensor located on said grinding means for sensing a load of said grinding means;
   b) a preservative pump for pumping preservative to said enzymatic digest medium;
   c) a variable frequency drive connected to said preservative pump for controlling the speed of said preservative pump;
   d) an a programmable logical computer circuit connected to said load sensor and said variable frequency drive, said circuit programmed to determine the speed of said preservative pump in relationship to said load.

* * * * *